(12) United States Patent
Burton et al.

(10) Patent No.: US 10,005,074 B2
(45) Date of Patent: Jun. 26, 2018

(54) MOLECULAR SIEVE MATERIAL, ITS SYNTHESIS AND USE

(71) Applicant: ExxonMobil Research and Engineering Company, Annandale, NJ (US)

(72) Inventors: Allen Wayne Burton, Stewartsville, NJ (US); Karl G. Strohmaier, Port Murray, NJ (US); Hilda B. Vroman, Piscataway, NJ (US); Yifeng Yun, Stockholm (SE); Xiaodong Zou, Sollentuna (SE); Wei Wan, Sollentuna (SE); Tom J. Willhammar, Solna (SE)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 0 days. days.

(21) Appl. No.: 15/465,716

(22) Filed: Mar. 22, 2017

(65) Prior Publication Data
US 2017/0252730 A1    Sep. 7, 2017

Related U.S. Application Data

(63) Continuation of application No. 14/188,954, filed on Feb. 25, 2014, now Pat. No. 9,636,666.
(Continued)

(51) Int. Cl.
*C01B 39/48* (2006.01)
*B01J 29/70* (2006.01)
(Continued)

(52) U.S. Cl.
CPC ............ *B01J 29/70* (2013.01); *C01B 37/007* (2013.01); *C01B 39/12* (2013.01); *C01B 39/48* (2013.01);
(Continued)

(58) Field of Classification Search
CPC ........... C01B 39/12; C01B 39/48; B01J 29/70
See application file for complete search history.

(56) References Cited

U.S. PATENT DOCUMENTS

| 4,585,639 A | 4/1986 | Szostak |
| 5,420,279 A | 5/1995 | Joly et al. |

(Continued)

FOREIGN PATENT DOCUMENTS

| WO | 2013019462 A1 | 2/2013 |
| WO | 2013028303 A1 | 2/2013 |

OTHER PUBLICATIONS

Lee, et al., "Synthesis and Characterization of ERI-Type UZM-12 Zeolites and Their Methanol-to-Olefin Performance", Journal of the American chemical Society, Sep. 22, 2010, pp. 12971-12982, vol. 132, No. 7, ACS Publications.
(Continued)

*Primary Examiner* — David M Brunsman
(74) *Attorney, Agent, or Firm* — Lisa K. Holthus (57) ABSTRACT

A molecular sieve material, EMM-25, having in its calcined form an X-ray diffraction pattern including the following peaks:

| d-spacing (Å) | Relative Intensity [100 × I/I(o)]% |
|---|---|
| 11.74-11.34 | 60-100 |
| 9.50-9.10 | 30-80 |
| 8.68-8.28 | 10-40 |
| 5.64-5.44 | 20-60 |
| 4.52-4.42 | 10-50 |
| 4.28-4.18 | 10-40 |
| 3.96-3.86 | 40-80 |
| 3.69-3.59 | 30-70 |

18 Claims, 4 Drawing Sheets

Related U.S. Application Data (60) Provisional application No. 61/807,470, filed on Apr. 2, 2013.

(51) Int. Cl.
   *C01B 37/00*    (2006.01)
   *C07C 7/13*    (2006.01)
   *C01B 39/12*    (2006.01)

(52) U.S. Cl.
   CPC ............ *C07C 7/13* (2013.01); *C07C 2531/02* (2013.01); *C07C 2601/16* (2017.05)

(56) References Cited

U.S. PATENT DOCUMENTS 9,636,666 B2 * 5/2017 Burton .................. C01B 37/007

2002/0010359 A1   1/2002   Kaita et al.
2009/0299105 A1   12/2009   Inoue et al.

OTHER PUBLICATIONS

Jackowski et al., "Diquaternary Ammonium compounds in Zeolite Synthesis: Cyclic and Polycyclic N-Heterocycles Connected by Methylene Chains", Journal of the American chemical Society, Jan. 7, 2009, pp. 1092-1100. vol. 131, No. 3, ACS Publications.

Moini et al., "The role of diquaternary cations as directing agents in zeolite synthesis", Zeolites, Sep. 1, 1994, pp. 504-511, vol. 14, No. 7, Elsevier Science Publishing.

PCT/US2014/018178 International Preliminary Report on Patentability dated Oct. 15, 2015.

* cited by examiner

MOLECULAR SIEVE MATERIAL, ITS SYNTHESIS AND USE

CROSS-REFERENCE TO RELATED APPLICATIONS

This application claims priority to U.S. patent application Ser. No. 14/188,954, filed Feb. 25, 2014, now U.S. Pat. No. 9,636,666, titled "Molecular Sieve Material, Its Synthesis and Use", the entirety of which is incorporated herein by reference, which claims the benefit of U.S. Provisional Application Ser. No. 61/807,470 filed on Apr. 2, 2013; which is also incorporated herein in its entirety by reference.

FIELD

This invention relates to a novel molecular sieve material, designated EMM-25, its synthesis, and its use as an adsorbent and/or a hydrocarbon conversion catalyst.

BACKGROUND

Molecular sieve materials, both natural and synthetic, have been demonstrated in the past to be useful as adsorbents and to have catalytic properties for various types of hydrocarbon conversion reactions. Certain molecular sieves, such as zeolites, AlPOs, and mesoporous materials, are ordered, porous crystalline materials having a definite crystalline structure as determined by X-ray diffraction (XRD). Within the crystalline molecular sieve material there are a large number of cavities which may be interconnected by a number of channels or pores. These cavities and pores are uniform in size within a specific molecular sieve material. Because the dimensions of these pores are such as to accept for adsorption molecules of certain dimensions while rejecting those of larger dimensions, these materials have come to be known as "molecular sieves" and are utilized in a variety of industrial processes.

Such molecular sieves, both natural and synthetic, include a wide variety of positive ion-containing crystalline silicates. These silicates can be described as rigid three-dimensional framework of $SiO_4$ and Periodic Table Group 13 element oxide (e.g., $AlO_4$). The tetrahedra are cross-linked by the sharing of oxygen atoms with the electrovalence of the tetrahedra containing the Group 13 element (e.g., aluminum or boron) being balanced by the inclusion in the crystal of a cation, for example a proton, an alkali metal or an alkaline earth metal cation. This can be expressed wherein the ratio of the Group 13 element (e.g., aluminum or boron) to the number of various cations, such as $H^+$, $Ca^{2+}/2$, $Sr^{2+}/2$, $Na^+$, $K^+$, or $Li^+$, is equal to unity.

Molecular sieves that find application in catalysis include any of the naturally occurring or synthetic crystalline molecular sieves. Examples of these molecular sieves include large pore zeolites, intermediate pore size zeolites, and small pore zeolites. These zeolites and their isotypes are described in "Atlas of Zeolite Framework Types", eds. Ch. Baerlocher, L. B. McCusker, D. H. Olson, Elsevier, Sixth Revised Edition, 2007, which is hereby incorporated by reference. A large pore zeolite generally has a pore size of at least about 6.5 to 7 Angstroms and includes LTL, MAZ, FAU, OFF, *BEA, and MOR framework type zeolites (IUPAC Commission of Zeolite Nomenclature). Examples of large pore zeolites include mazzite, offretite, zeolite L, zeolite Y, zeolite X, omega, and beta. An intermediate pore size zeolite generally has a pore size from about 4.5 Angstroms to less than about 7 Angstroms and includes, for example, MFI, MEL, EUO, MTT, MFS, AEL, AFO, HEU, FER, MWW, and TON framework type zeolites (IUPAC Commission of Zeolite Nomenclature). Examples of intermediate pore size zeolites include ZSM-5, ZSM-11, ZSM-22, MCM-22, silicalite 1, and silicalite 2. A small pore size zeolite has a pore size from about 3 Angstroms to less than about 5.0 Angstroms and includes, for example, CHA, ERI, KFI, LEV, SOD, and LTA framework type zeolites (IUPAC Commission of Zeolite Nomenclature). Examples of small pore zeolites include ZK-4, SAPO-34, SAPO-35, ZK-14, SAPO-42, ZK-21, ZK-22, ZK-5, ZK-20, zeolite A, chabazite, zeolite T, and ALPO-17.

According to the present invention, a new zeolite structure, designated EMM-25, has now been synthesized using at least one of the following four organic templates: N,N,N',N'-tetrahexyl-N,N'-dimethylbutane-1,4-diammonium, N,N'-dihexyl-N,N'-dipentyl-N,N'-dimethylbutane-1,4-diammonium, N,N,N',N'-tetrapentyl-N,N'-dimethylbutane-1,4-diammonium, N,N'-dipentyl-N,N'-dibutyl-N,N'-dimethylbutane-1,4-diammonium, and mixtures thereof.

SUMMARY

In one aspect, the invention relates to a molecular sieve material having, in its as-calcined form, an X-ray diffraction pattern including the following peaks in Table 1:

TABLE 1

| d-spacing (Å) | Relative Intensity [100 × I/I(o)]% |
|---|---|
| 11.74-11.34 | 60-100 |
| 9.50-9.10 | 30-80 |
| 8.68-8.28 | 10-40 |
| 5.64-5.44 | 20-60 |
| 4.52-4.42 | 10-50 |
| 4.28-4.18 | 10-40 |
| 3.96-3.86 | 40-80 |
| 3.69-3.59 | 30-70 |

In another aspect, the invention relates to a molecular sieve having a framework defined by the following connectivities for the tetrahedral (T) atoms in the unit cell in Table 2, the tetrahedral atoms (T) being connected by bridging atoms:

TABLE 2

| T atom | Connected to: |
|---|---|
| T1 | T3, T4, T33, T71 |
| T2 | T5, T48, T72, T82 |
| T3 | T1, T31, T47, T97 |
| T4 | T1, T5, T81, T106 |
| T5 | T2, T4, T55, T75 |
| T6 | T8, T9, T38, T76 |
| T7 | T10, T43, T77, T84 |
| T8 | T6, T36, T42, T98 |
| T9 | T6, T10, T83, T105 |
| T10 | T7, T9, T60, T80 |
| T11 | T13, T14, T23, T61 |
| T12 | T15, T58, T62, T86 |
| T13 | T11, T21, T57, T99 |
| T14 | T11, T15, T85, T108 |
| T15 | T12, T14, T45, T65 |
| T16 | T18, T19, T28, T66 |
| T17 | T20, T53, T67, T88 |
| T18 | T16, T26, T52, T100 |
| T19 | T16, T20, T87, T107 |
| T20 | T17, T19, T50, T70 |
| T21 | T13, T23, T24, T51 |
| T22 | T25, T52, T68, T90 |
| T23 | T11, T21, T67, T101 |

TABLE 2-continued

| T atom | Connected to: |
|---|---|
| T24 | T21, T25, T89, T110 |
| T25 | T22, T24, T55, T75 |
| T26 | T18, T28, T29, T56 |
| T27 | T30, T57, T63, T92 |
| T28 | T16, T26, T62, T102 |
| T29 | T26, T30, T91, T109 |
| T30 | T27, T29, T60, T80 |
| T31 | T3, T33, T34, T41 |
| T32 | T35, T42, T78, T94 |
| T33 | T1, T31, T77, T103 |
| T34 | T31, T35, T93, T112 |
| T35 | T32, T34, T45, T65 |
| T36 | T8, T38, T39, T46 |
| T37 | T40, T47, T73, T96 |
| T38 | T6, T36, T72, T104 |
| T39 | T36, T40, T95, T111 |
| T40 | T37, T39, T50, T70 |
| T41 | T31, T43, T44, T73 |
| T42 | T8, T32, T45, T86 |
| T43 | T7, T41, T71, T103 |
| T44 | T41, T45, T85, T112 |
| T45 | T15, T35, T42, T44 |
| T46 | T36, T48, T49, T78 |
| T47 | T3, T37, T50, T88 |
| T48 | T2, T46, T76, T104 |
| T49 | T46, T50, T87, T111 |
| T50 | T20, T40, T47, T49 |
| T51 | T21, T53, T54, T63 |
| T52 | T18, T22, T55, T82 |
| T53 | T17, T51, T61, T101 |
| T54 | T51, T55, T81, T110 |
| T55 | T5, T25, T52, T54 |
| T56 | T26, T58, T59, T68 |
| T57 | T13, T27, T60, T84 |
| T58 | T12, T56, T66, T102 |
| T59 | T56, T60, T83, T109 |
| T60 | T10, T30, T57, T59 |
| T61 | T11, T53, T63, T64 |
| T62 | T12, T28, T65, T94 |
| T63 | T27, T51, T61, T99 |
| T64 | T61, T65, T93, T108 |
| T65 | T15, T35, T62, T64 |
| T66 | T16, T58, T68, T69 |
| T67 | T17, T23, T70, T96 |
| T68 | T22, T56, T66, T100 |
| T69 | T66, T70, T95, T107 |
| T70 | T20, T40, T67, T69 |
| T71 | T1, T43, T73, T74 |
| T72 | T2, T38, T75, T90 |
| T73 | T37, T41, T71, T97 |
| T74 | T71, T75, T89, T106 |
| T75 | T5, T25, T72, T74 |
| T76 | T6, T48, T78, T79 |
| T77 | T7, T33, T80, T92 |
| T78 | T32, T46, T76, T98 |
| T79 | T76, T80, T91, T105 |
| T80 | T10, T30, T77, T79 |
| T81 | T4, T54, T89, T92 |
| T82 | T2, T52, T91, T113 |
| T83 | T9, T59, T90, T91 |
| T84 | T7, T57, T89, T114 |
| T85 | T14, T44, T93, T96 |
| T86 | T12, T42, T95, T115 |
| T87 | T19, T49, T94, T95 |
| T88 | T17, T47, T93, T116 |
| T89 | T24, T74, T81, T84 |
| T90 | T22, T72, T83, T113 |
| T91 | T29, T79, T82, T83 |
| T92 | T27, T77, T81, T114 |
| T93 | T34, T64, T85, T88 |
| T94 | T32, T62, T87, T115 |
| T95 | T39, T69, T86, T87 |
| T96 | T37, T67, T85, T116 |
| T97 | T3, T73, T103, T112 |
| T98 | T8, T78, T104, T111 |
| T99 | T13, T63, T101, T110 |
| T100 | T18, T68, T102, T109 |
| T101 | T23, T53, T99, T108 |
| T102 | T28, T58, T100, T107 |
| T103 | T33, T43, T97, T106 |
| T104 | T38, T48, T98, T105 |
| T105 | T9, T79, T104, T113 |
| T106 | T4, T74, T103, T114 |
| T107 | T19, T69, T102, T115 |
| T108 | T14, T64, T101, T116 |
| T109 | T29, T59, T100, T113 |
| T110 | T24, T54, T99, T114 |
| T111 | T39, T49, T98, T115 |
| T112 | T34, T44, T97, T116 |
| T113 | T82, T90, T105, T109 |
| T114 | T84, T92, T106, T110 |
| T115 | T86, T94, T107, T111 |
| T116 | T88, T96, T108, T112 |

Conveniently, the molecular sieve material can have a composition comprising the molar relationship: $X_2O_3$:(n) $YO_2$; wherein n can be at least 10, X can be a trivalent element, such as one or more of B, Al, Fe, and Ga (especially containing or being B), and Y can be a tetravalent element, such as one or more of Si, Ge, Sn, Ti, and Zr (especially containing or being Si).

In another aspect, the invention relates to a molecular sieve material having, in its as-synthesized form, an X-ray diffraction pattern including the following peaks in Table 3:

TABLE 3

| d-spacing (Å) | Relative Intensity [100 × I/I(o)]% |
|---|---|
| 11.77-11.37 | 30-80 |
| 9.51-9.11 | 20-70 |
| 8.67-8.27 | 5-30 |
| 5.64-5.44 | 10-40 |
| 4.50-4.40 | 30-80 |
| 4.28-4.18 | 30-80 |
| 3.95-3.85 | 60-100 |
| 3.70-3.60 | 50-90 |

Conveniently, the molecular sieve material can have a composition comprising the molar relationship: mQ:(n) $YO_2$: $X_2O_3$; wherein $0.004<m/n<0.04$, n can be at least 10, Q can be an organic structure directing agent, X can be a trivalent element, and Y can be a tetravalent element.

In embodiments, X may be one or more of B, Al, Fe, Ga, and Al; and Y may be one or more of Si, Ge, Sn, Ti, and Zr.

Conveniently, Q can comprise a cation of the formula:

$$R_1R_2(CH_3)N^+CH_2CH_2CH_2CH_2N^+(CH_3)R_1R_2$$

wherein $R_1$ and $R_2$ can be chosen independently from butyl, pentyl, and hexyl.

Optionally, Q can comprise or be a cation selected from the group consisting of N,N,N',N'-tetrahexyl-N,N'-dimethylbutane-1,4-diammonium ($C_4$ diquat of dihexylmethylamine), N,N'-dihexyl-N,N'-dipentyl-N,N'-dimethylbutane-1,4-diammonium ($C_4$ diquat of hexylpentylmethylamine), N,N,N',N'-tetrapentyl-N,N'-dimethylbutane-1,4-diammonium ($C_4$ diquat of dipentylmethylamine), N,N'-dipentyl-N,N'-dibutyl-N,N'-dimethylbutane-1,4-diammonium ($C_4$ diquat of pentylbutylmethylamine), and mixtures thereof.

In a further aspect, the invention relates to a process for producing the molecular sieve material as described herein, the process comprising: (i) preparing a synthesis mixture capable of forming said material, said mixture comprising water, a source of hydroxide ions, a source of an oxide of a tetravalent element Y, a source of a trivalent element X, optionally a source of halide ions $Z^-$, optionally a source of alkali metal ions M⁺, and a structure directing agent Q selected from the group consisting of N,N,N',N'-tetrahexyl-N,N'-dimethylbutane-1,4-diammonium cations, N,N'-dihexyl-N,N'-dipentyl-N,N'-dimethylbutane-1,4-diammonium cations, N,N,N',N'-tetrapentyl-N,N'-dimethylbutane-1,4-diammonium cations, N,N'-dipentyl-N,N'-dibutyl-N,N'-dimethylbutane-1,4-diammonium cations, and mixtures thereof, and said synthesis mixture having a composition, in terms of mole ratios, in the following amounts and/or ranges:

| | |
|---|---|
| YO₂/X₂O₃ | at least 2; |
| H₂O/YO₂ | 5 to 60; |
| OH⁻/YO₂ | 0.01 to 1; |
| Z⁻/YO₂ | 0 to 0.30; |
| M⁺/YO₂ | 0 to 0.40; and |
| Q/YO₂ | 0.03 to 1.0; |

(ii) heating said synthesis mixture under crystallization conditions including a temperature of from about 100° C. to about 200° C. and a time from about 1 to about 100 days until crystals of said material are formed; and (iii) recovering said crystalline material from said synthesis mixture.

Preferably, M⁺ can include or be a sodium and/or potassium ion. When Z⁻ is present, Z⁻ can advantageously include or be chloride ions.

Optionally, Q can be selected from N,N,N',N'-tetrapentyl-N,N'-dimethylbutane-1,4-diammonium cations, N,N,N',N'-tetrahexyl-N,N'-dimethylbutane-1,4-diammonium cations, and mixtures thereof. The structures of those cations are shown below.

N,N,N',N'-tetrapentyl-N,N'-dimethylbutane-1,4-diammonium

N,N,N',N'-tetrahexyl-N,N'-dimethylbutane-1,4-diammonium

In another aspect, the invention relates to a process of converting a feedstock comprising an organic compound to a conversion product which comprises contacting said feedstock at organic compound conversion conditions with a catalyst comprising an active form of the molecular sieve material as described herein.

DETAILED DESCRIPTION OF THE EMBODIMENTS

Described herein is a novel molecular sieve material, designated EMM-25, its synthesis in the presence of a structure directing agent, and its use, e.g., as an adsorbent and a catalyst for organic conversion reactions.

The novel molecular sieve material EMM-25 can be characterized by an X-ray diffraction pattern which, in its as-calcined form of the molecular sieve, can include at least the peaks shown below in Table 1 above and, in its as-synthesized form, can include at least the peaks shown in Table 3 above.

Optionally, the calcined form of the molecular sieve can have an XRD pattern including the additional peaks shown in Table 4 below.

TABLE 4

| d-spacing (Å) | Relative Intensity [100 × I/I(o)]% |
|---|---|
| 12.70-12.30 | 10-50 |
| 6.20-6.10 | 1-30 |
| 3.85-3.77 | 1-30 |

Optionally, the as-made form of the molecular sieve can have an XRD pattern including the additional peaks shown in Table 5 below.

TABLE 5

| d-spacing (Å) | Relative Intensity [100 × I/I(o)]% |
|---|---|
| 12.65-12.25 | 1-30 |
| 6.42-6.22 | 1-20 |
| 4.04-3.96 | 10-50 |
| 3.84-3.78 | 10-50 |

The EMM-25 may additionally or alternately be characterized, in its calcined form, by the framework defined by the connectivities of the tetrahedral (T) atoms shown in Table 2 above. Optionally, the tetrahedral atoms can include one or more elements selected from the group consisting of Li, Be, Al, P, Si, Ga, Ge, Zn, Cr, Mg, Fe, Co, Ni, Mn, As, In, Sn, Sb, Ti, and Zr (e.g., selected from the group consisting of Si, Ge, Sn, Ti, and Zr). Optionally, the bridging atoms include one or more elements selected from the group consisting of O, N, F, S, Se, and C. In such embodiments, the bridging atoms can preferably predominantly be oxygen atoms (e.g., at least 90% of the bridging atoms may be oxygen).

Optionally, the molecular sieve of the invention can be a borosilicate.

The X-ray diffraction data reported herein were collected with a PANalytical X-Pert Pro diffraction system, equipped with an X'Celerator detector, using copper K-alpha radiation and a fixed ~0.25 degrees divergence slit. The diffraction data were recorded by step-scanning at ~0.017 degrees of two-theta, where theta is the Bragg angle, and a counting time of about 2 seconds for each step. The interplanar (d-) spacings were calculated in Angstrom units, and the relative peak area intensities, $I/I_{(o)}$, of the peaks were determined using the MDI Jade peak profile fitting algorithm to approximately one-hundredth of the intensity of the strongest peak (above background). The peak intensities were uncorrected for Lorentz and polarization effects. It should be understood that diffraction data listed for each sample as a single peak may contain multiple overlapping peaks that, under certain conditions (such as differences in crystallographic changes), may appear as resolved (single local maximum) or partially resolved peaks. Typically, such conditions (e.g., crystallographic changes) can include minor changes in unit cell parameters and/or a change in crystal symmetry, without a corresponding change in the structure. These minor effects, including changes in relative intensities, can additionally or alternately occur as a result of differences in cation content, framework composition, nature and degree of pore filling, crystal size and shape, preferred orientation, thermal and/or hydrothermal history, or the like, or combinations thereof.

The molecular sieve material (EMM-25), in its calcined form, can have a chemical composition having the following molar relationship: $X_2O_3:(n)YO_2$; wherein n can be at least about 10 (such as from about 10 to about 200), X can be a trivalent element (such as one or more of B, Al, Fe, and Ga), and Y can be a tetravalent element (such as one or more of Si, Ge, Sn, Ti, and Zr). In one preferred embodiment, X can comprise or be B, and Y can comprise or be Si.

In its as-synthesized form, molecular sieve (EMM-25) can have a chemical composition having the following molar relationship: $mQ:(n)YO_2: X_2O_3$; wherein $0.004<m/n<0.04$, n can be at least 10, Q can be an organic structure directing agent, X can be a trivalent element (such as one or more of B, Al, Fe, and Ga), and Y can be a tetravalent element (such as one or more of Si, Ge, Sn, Ti, and Zr). Optionally, as in the calcined form, X can comprise or be B, and Y can comprise or be Si.

Suitable examples of the organic structure directing agent Q can include, but are not necessarily limited to, cations such as N,N,N',N'-tetrahexyl-N,N'-dimethylbutane-1,4-diammonium, N,N'-dihexyl-N,N'-dipentyl-N,N'-dimethylbutane-1,4-diammonium, N,N,N',N'-tetrapentyl-N,N'-dimethylbutane-1,4-diammonium, N,N'-dipentyl-N,N'-dibutyl-N,N'-dimethylbutane-1,4-diammonium, and mixtures thereof.

The Q component, which is typically associated with the as-synthesized form of molecular sieve EMM-25 as a result of its presence during crystallization, may be easily decomposed/removed by conventional post-crystallization methods, such as calcination.

The molecular sieve material EMM-25 can advantageously represent a thermally stable zeolite with a unique XRD pattern.

EMM-25 can be prepared from a synthesis mixture comprising water, a source of hydroxide ions, a source of an oxide of a tetravalent element Y, a source of a trivalent element X, optionally a source of halide ions $Z^-$, optionally a source of alkali metal ions $M^+$, such as sodium or potassium ions, and a directing agent Q described above. The synthesis mixture may have a composition, in terms of mole ratios of oxides, within the following amounts and/or ranges:

| Reactants | Useful | Preferred |
|---|---|---|
| $YO_2/X_2O_3$ | at least 1 | 2 to 14 |
| $H_2O/YO_2$ | 5 to 60 | 15 to 40 |
| $OH^-/YO_2$ | 0.01 to 1.0 | 0.10 to 0.60 |
| $Q/YO_2$ | 0.03 to 1.0 | 0.10 to 0.25 |
| $Z^-/YO_2$ | 0 to 0.30 | 0 to 0.20 |
| $M^+/YO_2$ | 0 to 0.4 | 0 to 0.10 |

In a preferred embodiment where $Z^-$ is present, $Z^-$ can comprise or be $Cl^-$. Additionally or alternately, in a preferred embodiment where $M^+$ is present, $M^+$ can comprise or be $Na^+$ and/or $K^+$.

Suitable sources of tetravalent element Y can depend on the element Y that is selected (e.g., silicon, germanium, strontium, titanium and zirconium). In embodiments where Y is silicon, suitable sources of silicon include colloidal suspensions of silica, precipitated silica alkali metal silicates, tetraalkyl orthosilicates, and fumed silicas. In embodiments where Y is germanium, germanium oxide may be used as an oxide source.

If present, suitable sources of trivalent element X depend on the element X that is selected (e.g., boron, aluminum, iron and gallium). In embodiments where X is boron, sources of boron include boric acid, sodium tetraborate and potassium tetraborate.

Q can preferably comprise or be a cation of the formula:

$$R_1R_2(CH_3)N^+CH_2CH_2CH_2CH_2N^+(CH_3)R_1R_2$$

wherein $R_1$ and $R_2$ can be chosen independently from butyl, pentyl and hexyl.

Nevertheless, suitable sources of the directing agent Q can include, but are not necessarily limited to, the hydroxides and/or salts of the relevant quaternary ammonium compounds. N,N,N',N'-tetrahexyl-N,N'-dimethylbutane-1,4-diammonium compounds can be readily synthesized, e.g., by the reaction of dihexylmethylamine with a 1,4-dihalobutane (such as 1,4-diiodobutane or 1,4-dibromobutane). N,N'-dihexyl-N,N'-dipentyl-N,N'-dimethylbutane-1,4-diammonium compounds can be readily synthesized, e.g., by the reaction of hexylpentylmethylamine with a 1,4-dihalobutane (such as 1,4-diiodobutane or 1,4-dibromobutane). N,N,N',N'-tetrapentyl-N',N'-dimethylbutane-1,4-diammonium compounds can be readily synthesised, e.g., by the reaction of dipentylmethylamine with a 1,4-dihalobutane (such as 1,4-diiodobutane or 1,4-dibromobutane). N,N'-dipentyl-N,N'-dibutyl-N,N'-dimethylbutane-1,4-diammonium compounds can be readily synthesized, e.g., by the reaction of pentylbutylmethylamine with a 1,4-dihalobutane (such as 1,4-diiodobutane or 1,4-dibromobutane).

Crystallization of EMM-25 can be carried out at either static or stirred conditions in a suitable reactor vessel, e.g., a polypropylene jar or a Teflon™-lined or stainless steel autoclave, at a temperature from about 100° C. to about 200°

C. (such as from about 150° C. to about 170° C.) for a time sufficient for crystallization to occur at the temperature used (e.g., from about 1 day to about 100 days, from about 1 day to about 50 days, or from about 2 days to about 20 days. Thereafter, the synthesized crystals can be separated from the liquid and advantageously recovered.

The synthesis may be aided by seeds from a previous synthesis of EMM-25, with the seeds, when present, suitably comprising an amount from about 0.01 ppm by weight to about 10000 ppm by weight, e.g., from about 100 ppm by weight to about 5000 ppm by weight, of the synthesis mixture.

To the extent desired and depending on the $X_2O_3/YO_2$ molar ratio of the material, any cations in the as-synthesized EMM-25 can be replaced in accordance with techniques well known in the art by ion exchange with other cations. When utilized, preferred replacing cations can include metal ions, hydrogen ions, hydrogen precursor (e.g., ammonium) ions, and mixtures thereof. When utilized, particularly preferred cations can include those that can tailor the catalytic activity for certain hydrocarbon conversion reactions, such as hydrogen, rare earth metals, and metals of Groups 2 to 15 of the Periodic Table of the Elements. As used herein, the numbering scheme for the Periodic Table Groups is as disclosed in Chemical and Engineering News, 63(5), 27 (1985).

The molecular sieve described herein may be subjected to treatment to remove a portion of or the entire amount of organic directing agent Q used in its synthesis. This can be conveniently done by thermal treatment (calcination), e.g., by heating the as-synthesized material to a temperature of at least about 370° C. for at least 1 minute (and generally not longer than 20 hours). While subatmospheric pressure can be employed for the thermal treatment, atmospheric pressure can typically be desired for reasons of convenience. The thermal treatment can be performed at a temperature up to about 1000° C., e.g., up to about 925° C. The thermally treated product, especially in its metal, hydrogen, and/or ammonium forms, can be particularly useful in the catalysis of certain organic, e.g., hydrocarbon, conversion reactions.

The molecular sieve described herein may be intimately combined with a hydrogenating component, such as molybdenum, rhenium, nickel, cobalt, chromium, manganese, or with a noble metal (such as platinum and/or palladium) where a hydrogenation-dehydrogenation function may be desired. Such component can be present in the composition by way of co-crystallization, by being exchanged into the composition (to the extent a Group 13 element, e.g., aluminum, is in the structure), by impregnation therein, by being intimately physically admixed therewith, or the like, or some combination thereof. Such component can be impregnated into/onto the molecular sieve, for example, in the case of platinum, by treating the silicate with a solution containing a platinum metal-containing ion. Thus, suitable platinum compounds for this purpose can include, but are not necessarily limited to, chloroplatinic acid, platinous chloride, various compounds containing the platinum amine complex, or mixtures/combinations thereof.

The molecular sieve of the present disclosure, when employed either as an adsorbent or as a catalyst, can advantageously be at least partially (or substantially) dehydrated, e.g., by heating to a temperature from about 100° C. to about 500° C. (such as from about 200° C. to about 370° C.) in an atmosphere (such as containing air, nitrogen, etc.) at atmospheric, subatmospheric, or superatmospheric pressures for an appropriate time, e.g., between about 30 minutes and about 48 hours. Dehydration can additionally or alternately be performed at room temperature (~20-25° C.), e.g., merely by placing the EMM-25 under vacuum (e.g., 0.01 torr or less), but a longer time may be required to sufficiently dehydrate.

The molecular sieve of the present disclosure may be used as an adsorbent or, particularly in its borosilicate form, as a catalyst for a wide variety of organic compound conversion processes, including many of present commercial/industrial importance. Examples of chemical conversion processes which can be effectively catalyzed by the crystalline material of this invention, by itself or in combination with one or more other catalytically active substances (including other crystalline catalysts), can include those requiring a catalyst with acid activity. Examples of organic conversion processes that may be catalyzed by EMM-25 can include, but are not necessarily limited to, (hydro)cracking, disproportionation, alkylation, isomerization/dewaxing, and the like, and combinations thereof.

As in the case of many catalysts, it may be desirable to incorporate EMM-25 with another component resistant to the temperatures and other conditions employed in organic conversion processes. Such components can include active and inactive materials and synthetic or naturally occurring zeolites, as well as inorganic materials such as clays, silica, and/or metal oxides such as alumina. The latter may be either naturally occurring or in the form of gelatinous precipitates or gels including mixtures of silica and other metal oxides. Use of a material in conjunction with EMM-25 (i.e., combined therewith or present during synthesis of the crystalline material, which can be in its active state) can tend to change the level of conversion and/or selectivity of the catalyst in certain organic conversion processes. Inactive materials can suitably serve as diluents, e.g., to control the amount of conversion in a given process, so that products can be obtained in an economic and orderly manner, such as without employing other means for controlling the rate of reaction. These materials may be incorporated into naturally occurring clays, e.g., bentonite and/or kaolin, to improve the crush strength of the catalyst under commercial operating conditions. Said materials, i.e., clays, oxides, etc., can function as binders for the catalyst. It can be desirable to provide a catalyst having good crush strength, because, in commercial use, it can be desirable to prevent/limit the catalyst from breaking down into powder-like materials (fines). These clay and/or oxide binders can be employed, e.g., solely to improve the crush strength of the catalyst.

Naturally occurring clays that can be composited with EMM-25 can include the montmorillonite and kaolin families, which families include the subbentonites, and the kaolins commonly known as Dixie, McNamee, Georgia and Florida clays, as well as others in which the main mineral constituent is halloysite, kaolinite, dickite, nacrite, or anauxite. Such clays can be used in the raw state (as originally mined) and/or initially subjected to calcination, acid treatment, and/or chemical modification. Binders useful for compositing with EMM-25 can additionally or alternately include inorganic oxides, such as silica, zirconia, titania, magnesia, beryllia, alumina, and mixtures thereof.

Additionally or alternatively to the foregoing materials, as desired, EMM-25 can be composited with a porous matrix material, such as silica-alumina, silica-magnesia, silica-zirconia, silica-thoria, silica-beryllia, silica-titania, as well as ternary compositions such as silica-alumina-thoria, silica-alumina-zirconia, silica-alumina-magnesia, silica-magnesia-zirconia, and mixtures or combinations thereof.

The relative proportions of EMM-25 and inorganic oxide matrix may vary widely, with the EMM-25 content typically ranging from about 1 wt % to about 90 wt %, or, particularly when the composite is prepared in the form of beads, from about 2 wt % to about 80 wt %, based on the total composite weight.

The invention can additionally or alternately include one or more of the following embodiments.

Embodiment 1

A molecular sieve material having, in its calcined form, an X-ray diffraction pattern including the peaks listed in Table 1.

Embodiment 2

A molecular sieve material having a framework defined by the connectivities for the tetrahedral (T) atoms in the unit cell listed in Table 2, the tetrahedral (T) atoms being connected by bridging atoms.

Embodiment 3

The molecular sieve material of embodiment 1 or embodiment 2, having a composition comprising the molar relationship: $(n)YO_2:X_2O_3$, wherein n is at least 10, X is a trivalent element (e.g., comprising one or more of B, Al, Fe, and Ga, such as comprising or being B), and Y is a tetravalent element (e.g., comprising one or more of Si, Ge, Sn, Ti, and Zr, such as comprising or being Si).

Embodiment 4

The molecular sieve material of embodiment 3, further comprising a noble metal and/or a salt of a noble metal.

Embodiment 5

A molecular sieve material having, in its as-synthesized form, an X-ray diffraction pattern including the peaks listed in Table 3.

Embodiment 6

The molecular sieve material of embodiment 5, having a composition comprising the molar relationship: $mQ:(n)YO_2: X_2O_3$, wherein $0.004<m/n<0.04$, n is at least 10, Q is an organic structure directing agent, X is a trivalent element (e.g., comprising one or more of B, Al, Fe, and Ga, such as comprising or being B), and Y is a tetravalent element (e.g., comprising one or more of Si, Ge, Sn, Ti, and Zr, such as comprising or being Si).

Embodiment 7

The molecular sieve material of embodiment 6, wherein Q is a cation of the formula: $R_1R_2(CH_3)N^+CH_2CH_2CH_2CH_2N^+(CH_3)R_1R_2$, wherein $R_1$ and $R_2$ are chosen independently from butyl, pentyl, and hexyl (e.g., wherein Q is a cation selected from the group consisting of N,N,N',N'-tetrahexyl-N,N'-dimethylbutane-1,4-diammonium, N,N'-dihexyl-N,N'-dipentyl-N,N'-dimethylbutane-1,4-diammonium, N,N,N',N'-tetrapentyl-N,N'-dimethylbutane-1,4-diammonium, N,N'-dipentyl-N,N'-dibutyl-N,N'-dimethylbutane-1,4-diammonium, and mixtures thereof).

Embodiment 8

A process for producing the molecular sieve material of any one of the previous embodiments, the process comprising: (i) preparing a synthesis mixture capable of forming said material, said mixture comprising water, a source of hydroxyl ions, a source of an oxide of a tetravalent element Y, a source of a trivalent element X, optionally a source of halide ions $Z^-$, optionally a source of alkali metal ions $M^+$, and a structure directing agent Q selected from the group consisting of N,N,N',N'-tetrahexyl-N,N'-dimethylbutane-1,4-diammonium cations, N,N'-dihexyl-N,N'-dipentyl-N,N'-dimethylbutane-1,4-diammonium cations, N,N,N',N'-tetrapentyl-N,N'-dimethylbutane-1,4-diammonium cations, N,N'-dipentyl-N,N'-dibutyl-N,N'-dimethylbutane-1,4-diammonium cations, and mixtures thereof, and said synthesis mixture having a composition, in terms of mole ratios, in the following amounts and/or ranges: $YO_2/X_2O_3$ of at least 1; $H_2O/YO_2$ of 5 to 60; $OH^-/YO_2$ of 0.01 to 1; $Z^-/YO_2$ of 0 to 0.30; $Q/YO_2$ of 0.03 to 1.0; and $M+/YO_2$ of 0 to 0.40; (ii) heating said synthesis mixture under crystallization conditions including a temperature from about 100° C. to about 200° C. and a time from about 1 day to about 100 days until crystals of said material are formed; and (iii) recovering said crystalline material from said synthesis mixture.

Embodiment 9

The process of embodiment 8, wherein the source of trivalent element X is one or more of boric acid, sodium tetraborate, and potassium tetraborate.

Embodiment 10

The process of embodiment 8 or embodiment 9, wherein the synthesis mixture has a pH from 8.0 to 10.5.

Embodiment 11

A process for converting a feedstock comprising an organic compound to a conversion product which comprises contacting said feedstock at organic compound conversion conditions with a catalyst comprising an active form of the molecular sieve material of any one of embodiments 1-7 and/or made according to the process of any one of embodiments 8-10.

The invention can now be more particularly described with reference to the following non-limiting Examples and the accompanying drawings.

EXAMPLES

Example 1

Figure 1:
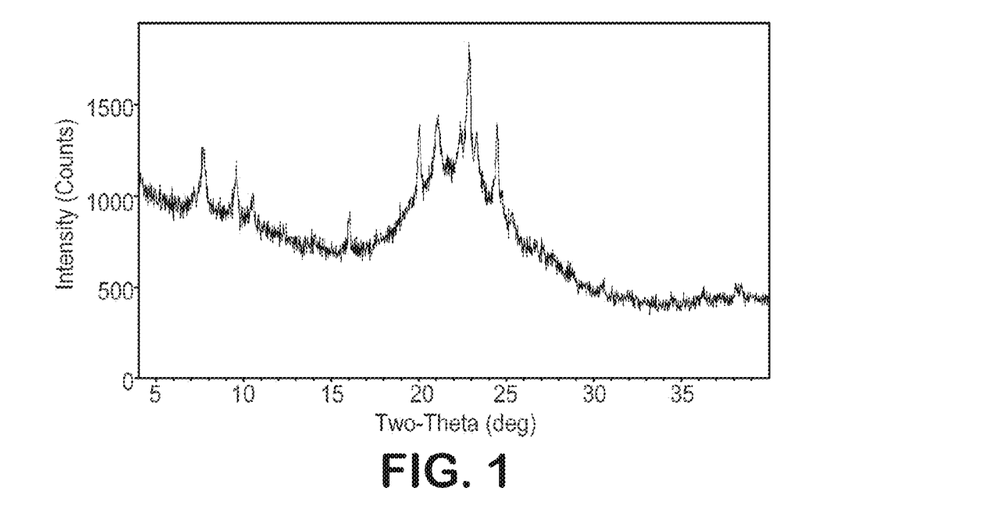
FIG. 1 shows the X-ray diffraction pattern of the synthesized zeolite of Example 1.

First, ~5.08 g of a hydroxide solution of the $C_4$ diquat of dihexylmethylamine (N,N,N',N'-tetrahexyl-N,N'-dimethylbutane-1,4-diammonium hydroxide; [OH]≈0.59 mmol/g) was mixed with ~2.22 g deionized water inside a Teflon™ liner for a ~23-mL steel Parr autoclave. Next about 0.19 g boric acid was added to the solution and mixed until nearly complete dissolution. Then about 2.25 g Ludox™ AS-40 (a colloidal suspension of ~40 mass % silica in water) was added to the solution, and ~1.50 g of ~1N HCl was added and mixed to create a relatively uniform suspension. The synthesis mixture had the following molar ratios: Si:B≈5; HCl:Si≈0.10; $H_2O$:Si≈35; and Q:Si≈0.1. The liner was then capped, sealed inside the ~23-mL autoclave, and heated at ~160° C. under tumbling conditions (~40 rpm). The reactor was removed after ~38 days, quenched, and the solid was isolated by filtration, washed, dried, and analyzed with powder XRD. FIG. 1 shows that the powder XRD of the product appeared to be a mixture of amorphous material and EMM-25.

Example 2

Figure 2:
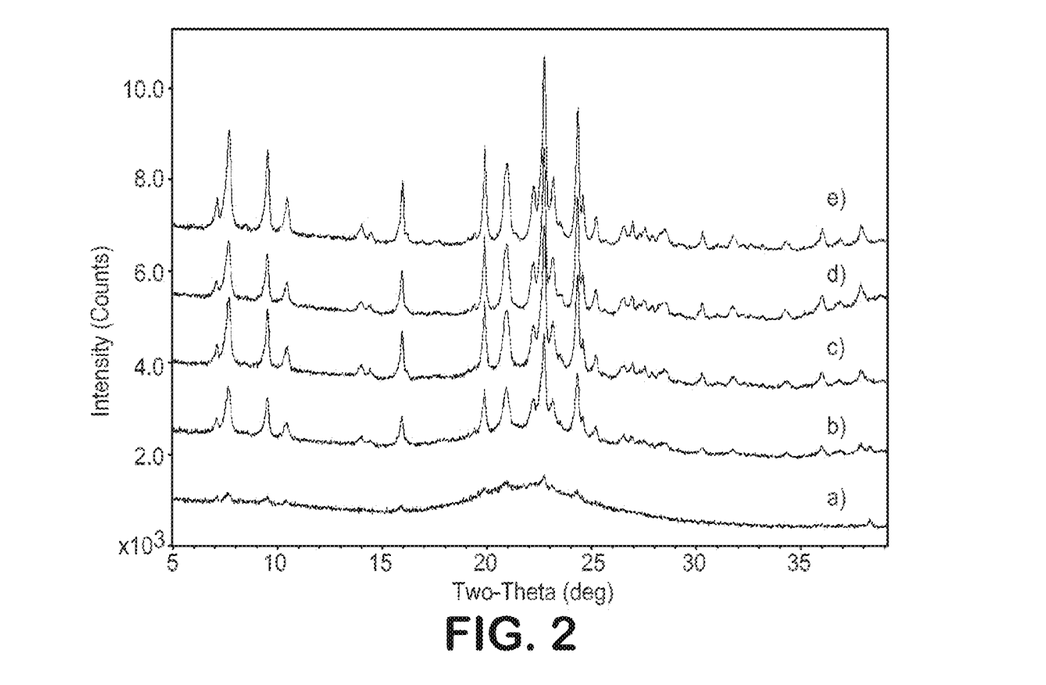
FIG. 2 shows the X-ray diffraction pattern of samples of the zeolite of Example 2 taken from the synthesis mixture: line a) ~17 days, line b) ~31 days, line c) ~38 days, line d) ~45 days, and line e) ~52 days.
Figure 3:
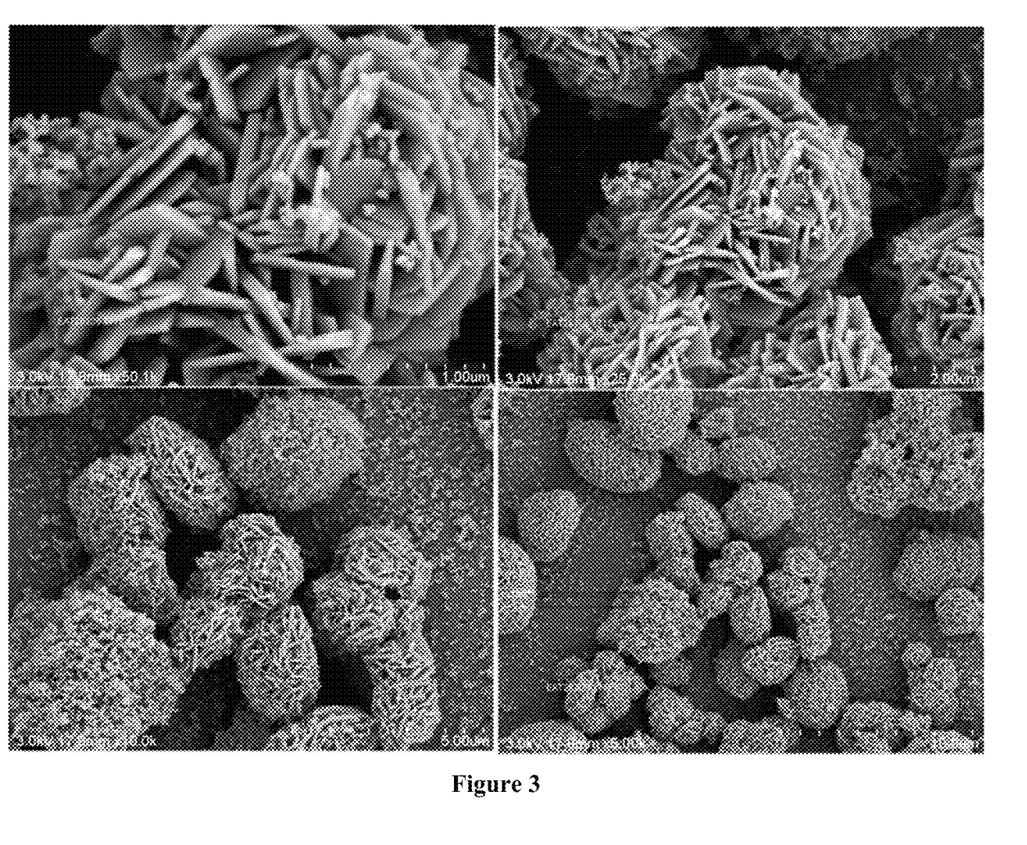
FIG. 3 shows Scanning Electron Microscopy (SEM) images of the zeolite of Example 2 taken from the synthesis mixture at ~38 days.

Example 1 was repeated using seeds (~0.04 g seeds/g $SiO_2$) of the EMM-25 product from Example 1. The reactor was removed after different heating periods and quenched. Aliquots of the gel mixture were removed, and the solids were isolated by filtration, washed, dried, and then analyzed with powder XRD. FIG. 2 shows that the synthesis appeared to be mostly complete after ~38 days of heating and appeared to be completely finished after ~52 days of heating. The powder XRD pattern of the final product could be indexed on a C-centered orthorhombic cell (a≈22.95 Å, b≈11.07 Å, and c≈24.85 Å). FIG. 3 shows SEM images of the product taken after ~38 days. The product appeared to show mostly a crystalline phase with a minor amorphous phase. The images appeared to show crystalline plates with edges of about 0.25 microns to about 1 micron in length and thicknesses of about 0.025 microns to about 0.1 microns.

The final product from Example 2 was heated inside a muffle furnace from ambient temperature (~20-25° C.) to about 400° C. at ~4° C./min under a nitrogen atmosphere, then heated to ~600° C. at ~4° C./min in air, and maintained at ~600° C. in air for about 2 hours. The calcined product was then measured with nitrogen physisorption, and the data were analyzed by the t-plot method, according to the method of Lippens, B. C. and deBoer, J. H., "Studies on pore systems in catalysts: V. The t method", *J. Catal.*, 4, 319 (1965). The determined micropore volume was ~0.15 cm$^3$/g, and the total BET surface area was ~419 m$^2$/g.

Example 3—Synthesis of N,N,N',N'-tetrahexyl-N, N'-dimethylbutane-1,4-diammonium hydroxide A diquaternary ammonium salt of N,N-dihexyl-N-methylamine was prepared by its reaction with 1,4-dibromobutane. To ~100 mL of acetone in a ~500-mL round bottom flask were added ~25.0 g of N,N-dihexyl-N-methylamine (Aldrich, ~0.125 mol) and ~12.3 g 1,4-dibromobutane (~0.057 mol). The resultant mixture was then refluxed for ~2 days. The solvent was then removed by rotary evaporation, and the product oil was extracted with ether to remove unreacted amine. The oil was then dried by rotary evaporation at ~80° C. under gradually reduced pressure (down to ~50 torr). The dibromide product was then ion-exchanged into the hydroxide form by dissolving it in a mixture of water and ethanol. To this solution was added approximately a two-fold excess of Dowex™ LC NG hydroxide exchange resin. The solution was recovered by filtration and extensive washing of the resin. The hydroxide solution was then extracted with ether to remove any amine impurities, and it was subsequently concentrated by rotary evaporation under gradually reduced pressure (down to ~50 torr) at ~65° C. The concentration of the aqueous solution was determined by titration with a standard solution of ~0.1N HCl.

Example 4—Synthesis of N,N'-dihexyl-N,N'-dipentyl-N,N'-dimethylbutane-1,4-diammonium hydroxide The N-pentyl-N-hexyl-N-methylamine was prepared by reductive amination of valeraldehyde (N-pentanal) with N-hexyl-N-methylamine. About 500 mL of tetrahydrofuran (THF) was placed in a ~1 L suction flask. About 28.4 g valeraldehyde (~0.34 mol) and then ~37.8 g N-hexyl-N-methylamine (~0.33 mol) were mixed into the THF. About 100 g of sodium triacetoxyborohydride powder was then added in ~5-10 g increments to the solution. During the addition, vigorous stirring was used to ensure that the powder clumped as little as possible at the bottom of the flask, thereby preventing efficient mixing of the suspension. After each addition of the sodium triacetoxyborohydride powder, adequate time was provided to form a relatively uniform slurry before the next addition of the powder. Once all of the powder had been added, the nitrogen flow was then turned on. After overnight mixing (~8-16 hours), the product was worked up by quenching the suspension with the slow addition of ~275 g of a ~24 mass % KOH (aqueous) solution. The product was then extracted from the resultant solution with pentane. The organic fraction was then collected with a separatory funnel and dried with anhydrous magnesium sulfate. The amine product was then isolated by rotary evaporation of the THF and pentane solvents under gradually reduced pressure (down to ~50 torr) to yield ~60.6 g of amine product (~95% pure by $^1$H NMR).

A diquaternary ammonium salt of N-pentyl-N-hexyl-N-methylamine was prepared by its reaction with 1,4-dibromobutane. To ~150 mL acetone in a ~500-mL round bottom flask were added ~60.6 g of N-pentyl-N-hexyl-N-methylamine (~0.32 mol) and ~31.9 g 1,4-dibromobutane (~0.15 mol). The resultant mixture was then refluxed for ~2 days. The solvent was then removed by rotary evaporation, and the product oil was extracted with ether to remove unreacted amine. The oil was then dried by rotary evaporation at ~80° C. under gradually reduced pressure (down to ~50 torr) to give ~84.1 g product. The dibromide product was then ion-exchanged into the hydroxide form by dissolving it in water and adding approximately a two-fold excess of Dowex™ LC NG hydroxide exchange resin. The solution was then recovered by filtration and extensive washing of the resin. The aqueous solution was then concentrated by rotary evaporation of the water under gradually reduced pressure (down to ~50 torr) at ~65° C. The aqueous solution concentration was determined by titration with a standard solution of ~0.1N HCl.

Example 5—Synthesis of N,N,N',N'-tetrapentyl-N,N'-dimethylbutane-1,4-diammonium hydroxide The di-N-pentyl-N-methylamine was prepared by reductive amination of formaldehyde with di-N-pentylamine using a procedure similar to that in Example 4. A diquaternary ammonium salt of di-N-pentyl-N-methylamine was prepared by its reaction with 1,4-dibromobutane using a procedure similar to that described in Example 4.

Example 6

Figure 4:
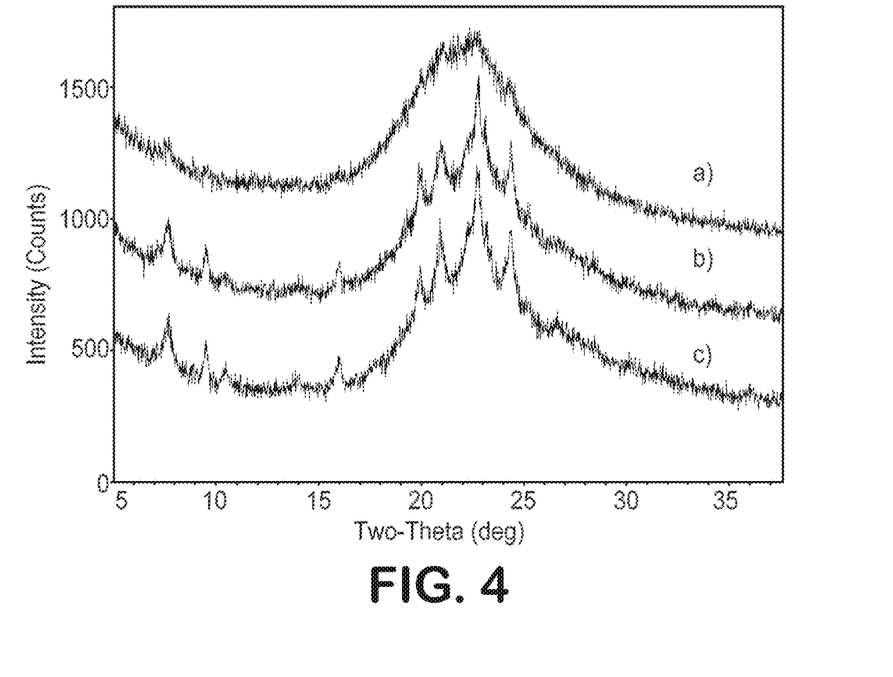
FIG. 4 shows the X-ray diffraction pattern of samples of the zeolite of Example 6 taken from the synthesis mixture at different times: line a) ~25 days, line b) ~35 days, and line c) ~49 days.

About 3.84 g of a hydroxide solution of N,N'-dihexyl-N,N'-dipentyl-N,N'-dimethylbutane-1,4-diammonium hydroxide (the $C_4$ diquat of N-hexyl-N-pentyl-N-methylamine; [OH]≈0.78 mmol/g) was mixed with ~3.42 g deionized water inside a Teflon™ liner for a ~23-mL steel Parr autoclave. Next ~0.19 g boric acid was added to the solution and mixed until nearly complete dissolution. Then ~2.25 g Ludox™ AS-40 was added to the solution, and ~1.50 g of ~1N HCl was added and mixed to create a relatively uniform suspension. Seeds (~0.04 g) of EMM-25 were added to the suspension. The liner was then capped, sealed inside the ~23-mL autoclave, and heated at ~160° C. under tumbling conditions (~40 rpm). The reactor was removed and quenched, and small quantities of product were sampled after ~25, ~35, and ~49 days of heating. FIG. 4 shows that EMM-25 appeared to be slowly crystallizing, although it appeared not to be complete after ~49 days.

Example 7

Figure 5:
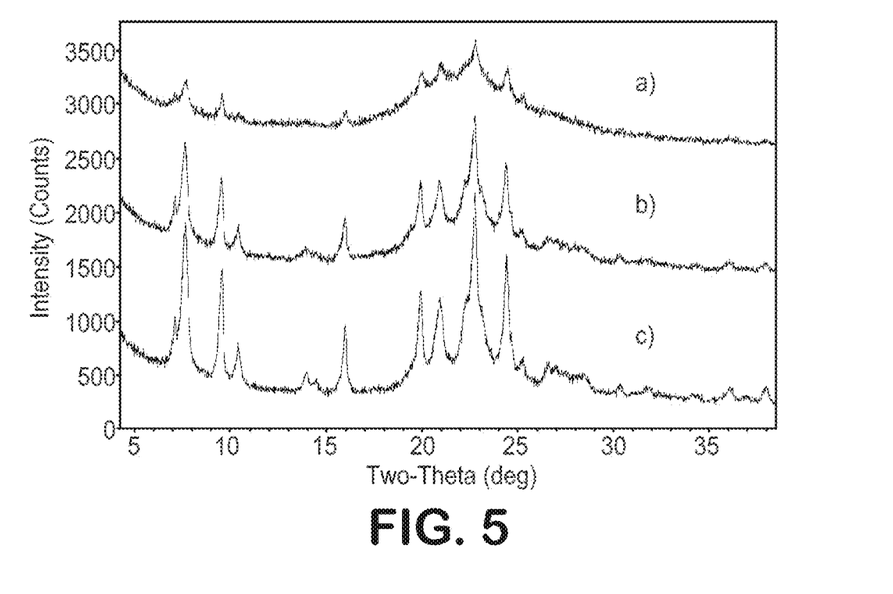
FIG. 5 shows the X-ray diffraction pattern of samples of the zeolite of Example 7 taken from the synthesis mixture at different times: line a) ~16 days, line b) ~23 days, and line c) ~27 days.

About 4.41 g of a hydroxide solution of N,N,N',N'-tetrapentyl-N,N'-dimethylbutane-1,4-diammonium hydroxide (the $C_4$ diquat of di-N-pentyl-N-methylamine; [OH]≈0.68 mmol/g) was mixed with ~2.81 g deionized water inside a Teflon™ liner for a ~23-mL steel Parr autoclave. Next ~0.19 g boric acid was added to the solution and mixed until nearly complete dissolution. Then ~2.25 g Ludox AS-40 was added to the mixture, and ~1.50 g of ~1N HCl was added and mixed to create a relatively uniform suspension. Seeds (~0.04 g) of EMM-25 were added to the suspension. The liner was then capped, sealed inside the ~23-mL autoclave, and heated at ~160° C. under tumbling conditions (~40 rpm). The reactor was removed and quenched, and small quantities of product were sampled after ~16, ~23, and ~27 days of heating. FIG. 5 shows that EMM-25 appeared to be nearly completely crystallized after ~27 days.

Example 8

Figure 6:
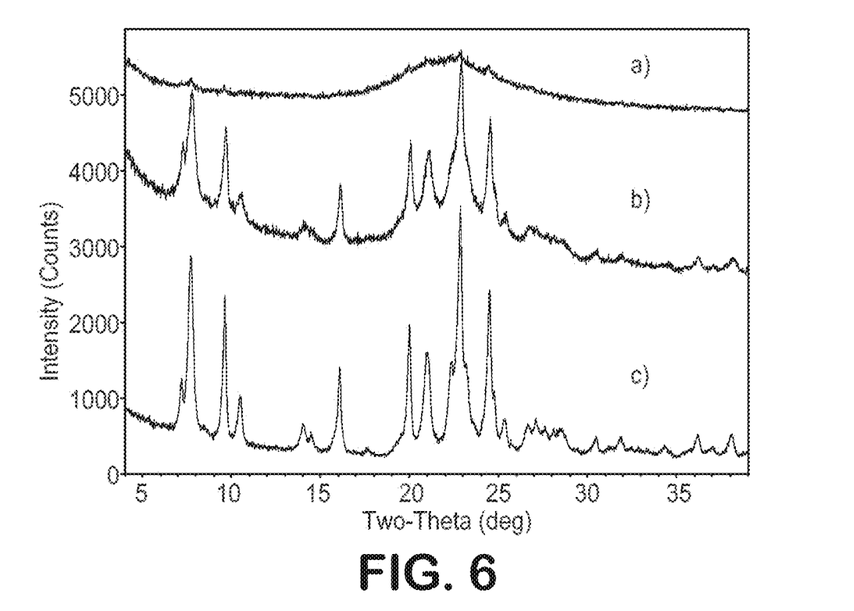
FIG. 6 shows the X-ray diffraction pattern of samples of the zeolite of Example 8 taken from the synthesis mixture at different times: line a) ~7 days, line b) ~14 days, and line c) ~21 days.

Example 7 was repeated, except using a ratio of NaOH/Si≈0.04. In Example 8, about 4.40 g of a hydroxide solution of N,N,N',N'-tetrapentyl-N,N'-dimethylbutane-1,4-diammonium hydroxide (the $C_4$ diquat of di-N-pentyl-N-methylamine; [OH]≈0.68 mmol/g) was mixed with ~2.24 g deionized water inside a Teflon™ liner for a ~23-mL steel Parr autoclave. To this solution was added ~0.60 g of ~1N NaOH. Next ~0.19 g boric acid was added to the solution and mixed until nearly complete dissolution. Then ~2.25 g Ludox™ AS-40 was added to the mixture, and ~1.50 g of ~1N HCl was added and mixed to create a relatively uniform suspension. Seeds (~0.04 g) of EMM-25 were added to the suspension. The liner was then capped, sealed inside the ~23-mL autoclave, and heated at ~160° C. under tumbling conditions (~40 rpm). The reactor was removed and quenched, and small quantities of product were sampled after ~7, ~14, and ~21 days of heating. FIG. 6 shows that the EMM-25 appeared to be completely crystallized after ~21 days.

Example 9

Figure 7:
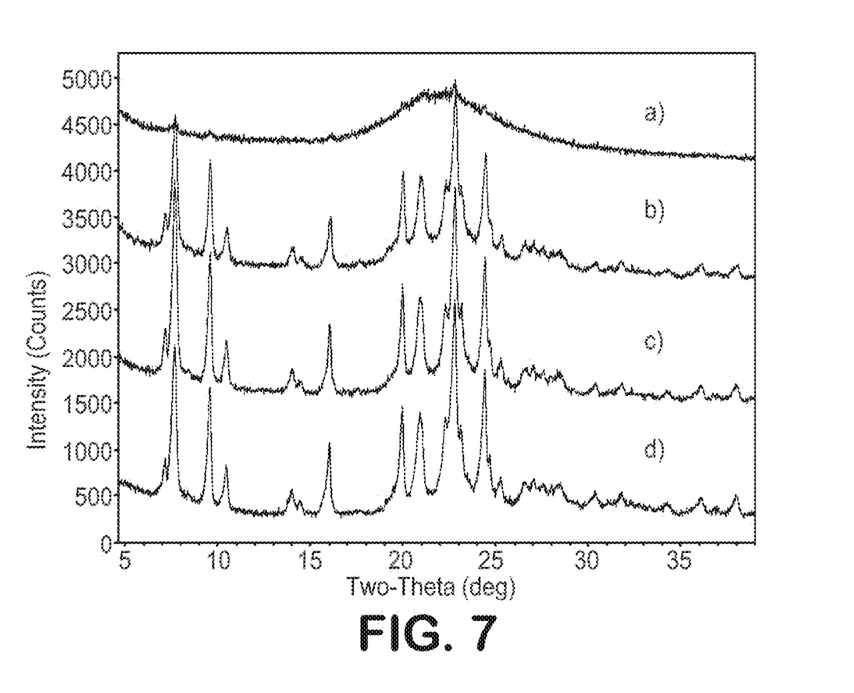
FIG. 7 shows the X-ray diffraction pattern of samples of the zeolite of Example 9 taken from the synthesis mixture at different times: line a) ~7 days, line b) ~21 days, line c) ~24 days, and line d) ~28 days.

Example 7 was repeated, except that the liner was heated at ~170° C. rather than at ~160° C. The reactor was removed and quenched, and small quantities of product were sampled after ~7, ~21, ~24, and ~28 days of heating. FIG. 7 shows that EMM-25 appeared to be completely or nearly completely crystallized after ~28 days.

Example 10

Example 7 was repeated, except that no HCl was added to the reaction. About 4.41 g of a hydroxide solution of N,N,N',N'-tetrapentyl-N,N'-dimethylbutane-1,4-diammonium hydroxide (the $C_4$ diquat of di-N-pentyl-N-methylamine; [OH]≈0.68 mmol/g) was mixed with ~4.27 g deionized water inside a Teflon™ liner for a ~23-mL steel Parr autoclave. Next ~0.19 g boric acid was added to the solution and mixed until nearly complete dissolution. Then ~2.25 g Ludox™ AS-40 was added to the mixture and mixed to create a relatively uniform suspension. Seeds (~0.04 g) of EMM-25 were added to the suspension. The liner was then capped, sealed inside the ~23-mL autoclave, and heated at ~160° C. under tumbling conditions (~40 rpm). After ~27 days of heating, the product appeared to be completely crystallized EMM-25, with a trace impurity of ZSM-5.

Example 11

About 2.63 g of a hydroxide solution of N,N,N',N'-tetrapentyl-N,N'-dimethylbutane-1,4-diammonium hydroxide (the $C_4$ diquat of di-N-pentyl-N-methylamine; [OH]≈0.68 mmol/g) and ~0.72 g of ~1N NaOH were mixed with ~5.20 g deionized water inside a Teflon™ liner for a ~23-mL steel Parr autoclave. Next ~0.093 g boric acid was dissolved in the solution. Then ~0.54 g Cabosil™ M-5 fumed silica was added to the mixture and mixed to create a relatively uniform suspension. Seeds (~0.04 g) of EMM-25 were added to the suspension. The liner was then capped, sealed inside the ~23-mL autoclave, and heated at ~160° C. under tumbling conditions (~40 rpm). After ~7 days of heating, the product appeared to be completely crystallized EMM-25, with a minor impurity of ZSM-5.

Example 12

Example 11 was repeated, except that ~1N KOH was used instead of ~1N NaOH. After ~7 days of heating, the product appeared to be completely crystallized EMM-25, with a minor impurity of ZSM-5.

Example 13

A reaction similar to Example 11 was repeated, except that no alkali hydroxide was used in the reaction. About 3.69 g of a hydroxide solution of N,N,N',N'-tetrapentyl-N,N'-dimethylbutane-1,4-diammonium hydroxide (the $C_4$ diquat of di-N-pentyl-N-methylamine; [OH]0.68 mmol/g) was mixed with ~7.93 g deionized water inside a Teflon™ liner for a ~23-mL steel Parr autoclave. Next ~0.13 g boric acid was dissolved in the solution. Then ~0.76 g Cabosil™ M-5 fumed silica was added to the mixture and mixed to create a relatively uniform suspension. Seeds (~0.04 g) of EMM-25 were added to the suspension. The liner was then capped, sealed inside the ~23-mL autoclave, and heated at ~160° C. under tumbling conditions (~40 rpm). After ~13 days of heating, the product was determined to be substantially pure EMM-25.

Example 14

Example 12 was repeated with half the amount of ~1N KOH. About 2.63 g of a hydroxide solution of N,N,N',N'-tetrapentyl-N,N'-dimethylbutane-1,4-diammonium hydroxide (the $C_4$ diquat of di-N-pentyl-N-methylamine; [OH]≈0.68 mmol/g) was mixed with ~5.55 g deionized water and ~0.36 g ~1N KOH inside a Teflon™ liner for a ~23-mL steel Parr autoclave. Next ~0.093 g boric acid was dissolved in the solution. Then ~0.54 g Cabosil™ M-5 fumed silica was added to the mixture and mixed to create a uniform suspension. Seeds (~0.04 g) of EMM-25 were added to the suspension. The liner was then capped, sealed inside the ~23-mL autoclave, and heated at ~160° C. under tumbling conditions (~40 rpm). After ~10 days of heating, the product was determined to be EMM-25, with a trace ZSM-5 impurity.

Example 15

Example 14 was repeated, except that the liner was heated at ~175° C. rather than at ~160° C. After ~11 days of heating, the product of Example 14 was determined to be EMM-25, with a trace layered phase impurity.

Characterization

A sample of as-synthesized EMM-25 yielded an XRD pattern having the following peaks (whose values are approximate):

| 2-Theta | d | [100 × I/I(o)]% |
|---|---|---|
| 7.10 | 12.45 | 13 |
| 7.64 | 11.57 | 47 |
| 8.46 | 10.45 | 2 |
| 9.50 | 9.31 | 38 |
| 10.44 | 8.47 | 17 |
| 14.00 | 6.32 | 8 |
| 14.47 | 6.11 | 4 |
| 15.87 | 5.58 | 9 |
| 15.98 | 5.54 | 27 |
| 16.19 | 5.47 | 4 |
| 17.64 | 5.02 | 1 |
| 19.14 | 4.63 | 3 |
| 19.43 | 4.57 | 5 |
| 19.92 | 4.45 | 50 |
| 20.96 | 4.23 | 43 |
| 22.26 | 3.99 | 27 |
| 22.76 | 3.9 | 100 |
| 23.20 | 3.83 | 28 |
| 23.53 | 3.78 | 8 |
| 24.37 | 3.65 | 72 |
| 24.65 | 3.61 | 21 |
| 25.25 | 3.52 | 15 |
| 25.71 | 3.46 | 2 |
| 26.58 | 3.35 | 8 |
| 27.01 | 3.3 | 13 |
| 27.34 | 3.26 | 5 |
| 27.60 | 3.23 | 8 |
| 27.96 | 3.19 | 5 |
| 28.29 | 3.15 | 4 |
| 28.56 | 3.12 | 8 |
| 29.26 | 3.05 | 2 |
| 30.36 | 2.94 | 8 |
| 31.13 | 2.87 | 3 |
| 31.83 | 2.81 | 8 |
| 32.30 | 2.77 | 2 |
| 32.72 | 2.74 | 3 |
| 34.35 | 2.61 | 3 |
| 36.09 | 2.49 | 11 |

The as-synthesized EMM-25 was calcined in a muffle furnace by heating in a nitrogen stream from ambient temperature (~20-25° C.) to ~400° C. over a ~2-hour period, maintaining this temperature for ~15 minutes, switching the gas stream to air, increasing the temperature from ~400° C. to ~600° C. over a ~2-hour period, maintaining the temperature at ~600° C. for ~2 hours, and then allowing the furnace to cool to ambient temperature (~20-25° C.). A sample of as-calcined EMM-25 yielded an XRD pattern having the following peaks (whose values are approximate):

| 2-Theta | d | [100 × I/I(o)]% |
|---|---|---|
| 7.07 | 12.5 | 35 |
| 7.66 | 11.54 | 100 |
| 8.48 | 10.42 | 2 |
| 9.51 | 9.3 | 56 |
| 10.43 | 8.48 | 27 |
| 14.06 | 6.3 | 12 |
| 14.5 | 6.1 | 9 |
| 15.44 | 5.73 | 2 |
| 15.99 | 5.54 | 40 |
| 16.19 | 5.47 | 6 |
| 19.29 | 4.6 | 3 |
| 19.87 | 4.47 | 34 |
| 20.99 | 4.23 | 23 |
| 22.33 | 3.98 | 14 |
| 22.71 | 3.91 | 59 |
| 23.25 | 3.82 | 18 |
| 23.59 | 3.77 | 7 |
| 24.4 | 3.64 | 48 |
| 24.69 | 3.6 | 8 |
| 25.22 | 3.53 | 8 |
| 25.64 | 3.47 | 2 |
| 26.5 | 3.36 | 7 |
| 26.79 | 3.32 | 1 |
| 27 | 3.3 | 3 |
| 27.37 | 3.26 | 2 |
| 27.6 | 3.23 | 7 |
| 27.92 | 3.19 | 4 |
| 28.36 | 3.14 | 5 |
| 28.6 | 3.12 | 8 |
| 29.3 | 3.05 | 2 |
| 30.36 | 2.94 | 5 |
| 31.88 | 2.8 | 5 |
| 32.37 | 2.76 | 2 |
| 32.64 | 2.74 | 2 |
| 33.26 | 2.69 | 2 |
| 34.42 | 2.6 | 4 |
| 35.99 | 2.49 | 5 |

A sample of as-calcined EMM-25 was further tested for its capacity to adsorb n-hexane, 2,2-dimethylbutane, and mesitylene. All the materials were thermally treated at ~500°

C. for a time sufficient to substantially dehydrate the materials and/or to remove any adsorbed species prior to doing the sorption test; the hydrocarbon was then introduced through a sparger to saturate the nitrogen stream. Each sorbate was adsorbed at a different temperature: hexane at ~90° C., 2,2-dimethylbutane at ~120° C., and mesitylene at ~100° C. The results are summarized below:

| | |
|---|---|
| n-hexane | ~80.6 mg/g |
| 2,2-dimethylbutane | ~51.3 mg/g |
| mesitylene | ~22.2 mg/g |

A sample of as-synthesized EMM-25 was also analyzed for boron content by $^{12}B$ NMR by comparison of signal intensity with a standard of known boron concentration. The boron concentration in the EMM-25 was found to be ~0.63% by mass.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for producing a molecular sieve material having, in its calcined form, an X-ray diffraction pattern including the following peaks:

| d-spacing (Å) | Relative Intensity 100 × I/I(o)]% |
|---|---|
| 11.74-11.34 | 60-100 |
| 9.50-9.10 | 30-80 |
| 8.68-8.28 | 10-40 |
| 5.64-5.44 | 20-60 |
| 4.52-4.42 | 10-50 |
| 4.28-4.18 | 10-40 |
| 3.96-3.86 | 40-80 |
| 3.69-3.59 | 30-70 | the process comprising:
(i) preparing a synthesis mixture capable of forming said material, said mixture comprising water, a source of hydroxyl ions, a source of an oxide of a tetravalent element Y, a source of a trivalent element X, optionally a source of halide ions $Z^-$, optionally a source of alkali metal ions $M^+$, and a structure directing agent Q selected from the group consisting of N,N,N',N'-tetrahexyl-N,N'-dimethylbutane-1,4-diammonium cations, N, N'-dihexyl-N,N'-dipentyl-N,N'-dimethylbutane-1,4-diammonium cations, N,N,N',N'-tetrapentyl-N,N'-dimethylbutane-1,4-diammonium cations, N,N'-dipentyl-N,N'-dibutyl-N,N'-dimethylbutane-1,4-diammonium cations, and mixtures thereof, and said synthesis mixture having a composition, in terms of mole ratios, in the following amounts and/or ranges:

| | |
|---|---|
| $YO_2/X_2O_3$ | at least 1; |
| $H_2O/YO_2$ | 5 to 60; |
| $OH^-/YO_2$ | 0.01 to 1; |
| $Z^-/YO_2$ | 0 to 0.30; |
| $Q/YO_2$ | 0.03 to 1.0; and |
| $M^+/YO_2$ | 0 to 0.40; |

(ii) heating said synthesis mixture under crystallization conditions including a temperature from about 100° C. to about 200° C. and a time from about 1 day to about 100 days until crystals of said material are formed; and
(iii) recovering said crystalline material from said synthesis mixture.

2. The process of claim 1, wherein the molecular sieve has a composition comprising the molar relationship: $(n)YO_2$: $X_2O_3$, wherein n is at least 10, X is a trivalent element, and Y is a tetravalent element.

3. The process of claim 2, wherein X comprises one or more of B, Al, Fe, and Ga, and wherein Y comprises one or more of Si, Ge, Sn, Ti, and Zr.

4. The process of claim 2, wherein X is boron and Y is silicon.

5. The process of claim 4, wherein the source of trivalent element X is one or more of boric acid, sodium tetraborate, and potassium tetraborate.

6. The process of claim 1, wherein the synthesis mixture has a pH from 8.0 to 10.5.

7. A process for producing a molecular sieve material having a framework defined by the following connectivities for the tetrahedral (T) atoms in the unit cell, the tetrahedral (T) atoms being connected by bridging atoms:

| T atom | Connected to: |
|---|---|
| T1 | T3, T4, T33, T71 |
| T2 | T5, T48, T72, T82 |
| T3 | T1, T31, T47, T97 |
| T4 | T1, T5, T81, T106 |
| T5 | T2, T4, T55, T75 |
| T6 | T8, T9, T38, T76 |
| T7 | T10, T43, T77, T84 |
| T8 | T6, T36, T42, T98 |
| T9 | T6, T10, T83, T105 |
| T10 | T7, T9, T60, T80 |
| T11 | T13, T14, T23, T61 |
| T12 | T15, T58, T62, T86 |
| T13 | T11, T21, T57, T99 |
| T14 | T11, T15, T85, T108 |
| T15 | T12, T14, T45, T65 |
| T16 | T18, T19, T28, T66 |
| T17 | T20, T53, T67, T88 |
| T18 | T16, T26, T52, T100 |
| T19 | T16, T20, T87, T107 |
| T20 | T17, T19, T50, T70 |
| T21 | T13, T23, T24, T51 |
| T22 | T25, T52, T68, T90 |
| T23 | T11, T21, T67, T101 |
| T24 | T21, T25, T89, T110 |
| T25 | T22, T24, T55, T75 |
| T26 | T18, T28, T29, T56 |
| T27 | T30, T57, T63, T92 |
| T28 | T16, T26, T62, T102 |
| T29 | T26, T30, T91, T109 |
| T30 | T27, T29, T60, T80 |
| T31 | T3, T33, T34, T41 |
| T32 | T35, T42, T78, T94 |
| T33 | T1, T31, T77, T103 |
| T34 | T31, T35, T93, T112 |
| T35 | T32, T34, T45, T65 |
| T36 | T8, T38, T39, T46 |
| T37 | T40, T47, T73, T96 |
| T38 | T6, T36, T72, T104 |
| T39 | T36, T40, T95, T111 |
| T40 | T37, T39, T50, T70 |
| T41 | T31, T43, T44, T73 |
| T42 | T8, T32, T45, T86 |
| T43 | T7, T41, T71, T103 |
| T44 | T41, T45, T85, T112 |
| T45 | T15, T35, T42, T44 |
| T46 | T36, T48, T49, T78 |

-continued

| T atom | Connected to: |
|---|---|
| T47 | T3, T37, T50, T88 |
| T48 | T2, T46, T76, T104 |
| T49 | T46, T50, T87, T111 |
| T50 | T20, T40, T47, T49 |
| T51 | T21, T53, T54, T63 |
| T52 | T18, T22, T55, T82 |
| T53 | T17, T51, T61, T101 |
| T54 | T51, T55, T81, T110 |
| T55 | T5, T25, T52, T54 |
| T56 | T26, T58, T59, T68 |
| T57 | T13, T27, T60, T84 |
| T58 | T12, T56, T66, T102 |
| T59 | T56, T60, T83, T109 |
| T60 | T10, T30, T57, T59 |
| T61 | T11, T53, T63, T64 |
| T62 | T12, T28, T65, T94 |
| T63 | T27, T51, T61, T99 |
| T64 | T61, T65, T93, T108 |
| T65 | T15, T35, T62, T64 |
| T66 | T16, T58, T68, T69 |
| T67 | T17, T23, T70, T96 |
| T68 | T22, T56, T66, T100 |
| T69 | T66, T70, T95, T107 |
| T70 | T20, T40, T67, T69 |
| T71 | T1, T43, T73, T74 |
| T72 | T2, T38, T75, T90 |
| T73 | T37, T41, T71, T97 |
| T74 | T71, T75, T89, T106 |
| T75 | T5, T25, T72, T74 |
| T76 | T6, T48, T78, T79 |
| T77 | T7, T33, T80, T92 |
| T78 | T32, T46, T76, T98 |
| T79 | T76, T80, T91, T105 |
| T80 | T10, T30, T77, T79 |
| T81 | T4, T54, T89, T92 |
| T82 | T2, T52, T91, T113 |
| T83 | T9, T59, T90, T91 |
| T84 | T7, T57, T89, T114 |
| T85 | T14, T44, T93, T96 |
| T86 | T12, T42, T95, T115 |
| T87 | T19, T49, T94, T95 |
| T88 | T17, T47, T93, T116 |
| T89 | T24, T74, T81, T84 |
| T90 | T22, T72, T83, T113 |
| T91 | T29, T79, T82, T83 |
| T92 | T27, T77, T81, T114 |
| T93 | T34, T64, T85, T88 |
| T94 | T32, T62, T87, T115 |
| T95 | T39, T69, T86, T87 |
| T96 | T37, T67, T85, T116 |
| T97 | T3, T73, T103, T112 |
| T98 | T8, T78, T104, T111 |
| T99 | T13, T63, T101, T110 |
| T100 | T18, T68, T102, T109 |
| T101 | T23, T53, T99, T108 |
| T102 | T28, T58, T100, T107 |
| T103 | T33, T43, T97, T106 |
| T104 | T38, T48, T98, T105 |
| T105 | T9, T79, T104, T113 |
| T106 | T4, T74, T103, T114 |
| T107 | T19, T69, T102, T115 |
| T108 | T14, T64, T101, T116 |
| T109 | T29, T59, T100, T113 |
| T110 | T24, T54, T99, T114 |
| T111 | T39, T49, T98, T115 |
| T112 | T34, T44, T97, T116 |
| T113 | T82, T90, T105, T109 |
| T114 | T84, T92, T106, T110 |
| T115 | T86, T94, T107, T111 |
| T116 | T88, T96, T108, T112 | the process comprising:
(i) preparing a synthesis mixture capable of forming said material, said mixture comprising water, a source of hydroxyl ions, a source of an oxide of a tetravalent element Y, a source of a trivalent element X, optionally a source of halide ions $Z^-$, optionally a source of alkali metal ions $M^+$, and a structure directing agent Q selected from the group consisting of N,N,N',N'-tetrahexyl-N,N'-dimethylbutane-1,4-diammonium cations, N,N'-dihexyl-N,N'-dipentyl-N,N'-dimethylbutane-1,4-diammonium cations, N,N,N',N'-tetrapentyl-N,N'-dimethylbutane-1,4-diammonium cations, N,N'-dipentyl-N,N'-dibutyl-N,N'-dimethylbutane-1,4-diammonium cations, and mixtures thereof, and said synthesis mixture having a composition, in terms of mole ratios, in the following amounts and/or ranges:

| | |
|---|---|
| $YO_2/X_2O_3$ | at least 1; |
| $H_2O/YO_2$ | 5 to 60; |
| $OH^-/YO_2$ | 0.01 to 1; |
| $Z^-/YO_2$ | 0 to 0.30; |
| $Q/YO_2$ | 0.03 to 1.0; and |
| $M^+/YO_2$ | 0 to 0.40 |

(ii) heating said synthesis mixture under crystallization conditions including a temperature from about 100° C. to about 200° C. and a time from about 1 day to about 100 days until crystals of said material are formed; and
(iii) recovering said crystalline material from said synthesis mixture.

8. The process of claim 7, wherein the molecular sieve has a composition comprising the molar relationship: $(n)YO_2$: $X_2O_3$, wherein n is at least 10, X is a trivalent element, and Y is a tetravalent element.

9. The process of claim 8, wherein X includes one or more of B, Al, Fe, and Ga, and wherein Y includes one or more of Si, Ge, Sn, Ti, and Zr.

10. The process of claim 8, wherein X is boron and Y is silicon.

11. The process of claim 10, wherein the source of trivalent element X is one or more of boric acid, sodium tetraborate, and potassium tetraborate.

12. The process of claim 7, wherein the synthesis mixture has a pH from 8.0 to 10.5.

13. A process for producing a molecular sieve material having, in its as-synthesized form, an X-ray diffraction pattern including the following peaks:

| d-spacing (Å) | Relative Intensity [100 × I/I(o)]% |
|---|---|
| 11.77–11.37 | 30–80 |
| 9.51–9.11 | 20–70 |
| 8.67–8.27 | 5–30 |
| 5.64–5.44 | 10–40 |
| 4.50–4.40 | 30–80 |
| 4.28–4.18 | 30–80 |
| 3.95–3.85 | 60–100 |
| 3.70–3.60 | 50–90 | the process comprising:
(i) preparing a synthesis mixture capable of forming said material, said mixture comprising water, a source of hydroxyl ions, a source of an oxide of a tetravalent element Y, a source of a trivalent element X, optionally a source of halide ions $Z^-$, optionally a source of alkali metal ions $M^+$, and a structure directing agent Q selected from the group consisting of N,N,N',N'-tetrahexyl-N,N'-dimethylbutane-1,4-diammonium cations, N,N'-dihexyl-N,N'-dipentyl-N,N'-dimethylbutane-1,4-diammonium cations, N,N,N',N'-tetrapentyl-N,N'-dimethylbutane-1,4-diammonium cations, N,N'-dipentyl-N,N'-dibutyl-N,N'-dimethylbutane-1,4-diammonium cations, and mixtures thereof, and said synthesis mixture having a composition, in terms of mole ratios, in the following amounts and/or ranges:

| | |
|---|---|
| $YO_2/X_2O_3$ | at least 1; |
| $H_2O/YO_2$ | 5 to 60; |
| $OH^-/YO_2$ | 0.01 to 1; |
| $Z^-/YO_2$ | 0 to 0.30; |
| $Q/YO_2$ | 0.03 to 1.0; and |
| $M^+/YO_2$ | 0 to 0.40 |

(ii) heating said synthesis mixture under crystallization conditions including a temperature from about 100° C. to about 200° C. and a time from about 1 day to about 100 days until crystals of said material are formed; and (iii) recovering said crystalline material from said synthesis mixture.

14. The process of claim 13, wherein the molecular sieve has a composition comprising the molar relationship: (n)$YO_2$:$X_2O_3$, wherein n is at least 10, X is a trivalent element, and Y is a tetravalent element.

15. The process of claim 14, wherein X comprises one or more of B, Al, Fe, and Ga, and wherein Y comprises one or more of Si, Ge, Sn, Ti, and Zr.

16. The process of claim 14, wherein X is boron and Y is silicon.

17. The process of claim 16, wherein the source of trivalent element X is one or more of boric acid, sodium tetraborate, and potassium tetraborate.

18. The process of claim 13, wherein the synthesis mixture has a pH from 8.0 to 10.5.

* * * * *